United States Patent [19]

Kontos

[11] 4,245,635
[45] Jan. 20, 1981

[54] CATHETER ASSEMBLY FOR INTERMITTENT INTRAVENOUS USE

[75] Inventor: Stavros B. Kontos, Oakland, N.J.

[73] Assignee: Jelco Laboratories, Raritan, N.J.

[21] Appl. No.: 7,136

[22] Filed: Jan. 29, 1979

[51] Int. Cl.³ ............................................. A61M 5/00
[52] U.S. Cl. ................................ 128/214.4; 128/274; 251/149.1
[58] Field of Search ............... 128/214 R, 214.4, 221, 128/274, 350 V; 251/149.1, 149.3

[56] References Cited

U.S. PATENT DOCUMENTS

| | | | |
|---|---|---|---|
| 1,173,620 | 2/1916 | Thompson | 251/149.1 |
| 2,538,662 | 1/1951 | Abbott | 128/214 R |
| 3,557,778 | 1/1971 | Hughes | 128/766 |
| 3,895,632 | 7/1975 | Plowiecki | 128/214.4 |
| 3,896,853 | 7/1975 | Bernhard | 128/766 |
| 4,106,491 | 8/1978 | Guerra | 128/214 R X |

*Primary Examiner*—Dalton L. Truluck
*Attorney, Agent, or Firm*—Donal B. Tobin

[57] ABSTRACT

An intravenous catheter assembly comprises a catheter having an elongate hollow tube and a hub connected to said tube. The hub has an interior cavity communicating with the lumen of the tube and also includes an aperture communicating with the cavity. A needle is slidably positioned in the aperture and the lumen of the tube so that its pointed end protrudes slightly beyond the distal end of the catheter tube. An operable valve includes a closure portion located in the cavity and is adapted to close the interior entrance of the aperture under the influence of fluid flowing into the cavity from the lumen after the needle is withdrawn. The operable valve also includes an activating portion located outside the exterior entrance of the aperture and is adapted to be moved generally axially to thereby move the closure portion away from the aperture and open the same for fluid flow into the cavity.

8 Claims, 5 Drawing Figures

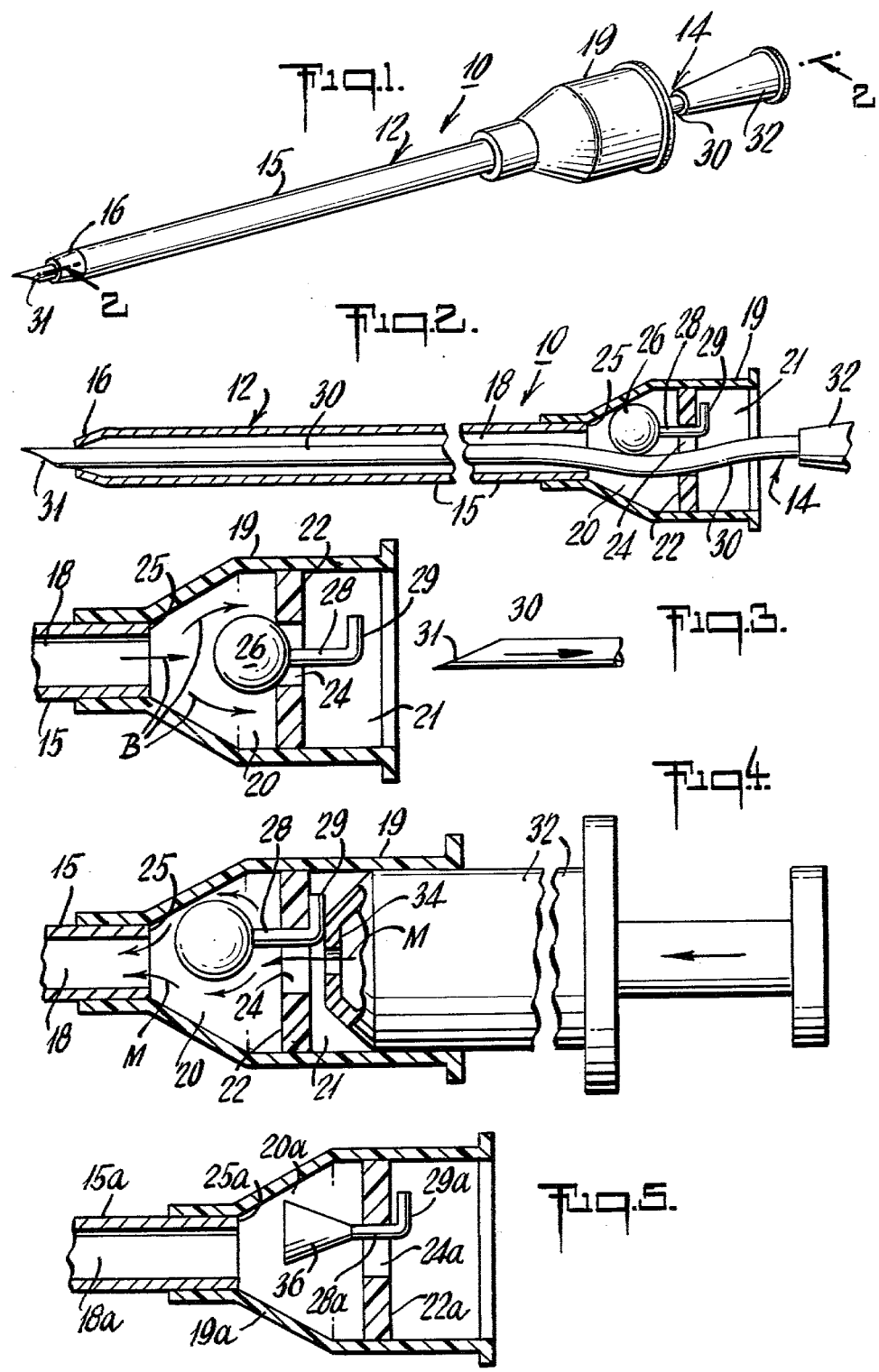

CATHETER ASSEMBLY FOR INTERMITTENT INTRAVENOUS USE

BACKGROUND OF THE INVENTION

The present invention relates to an intravenous catheter for medical purposes and, more particularly, concerns an intravenous catheter assembly useful for periodic or intermittent delivery of medication to a patient.

Intravenous catheters through which medication is delivered to a patient are oftentimes expected to be used on more than one occasion for the periodic delivery of the medication to the patient. When using one intravenous catheter, the initial venipuncture and medication delivery are made and then the catheter remains inserted in the patient's vein. Proper closure elements are employed in these type catheters to prevent blood or other body fluids from backflowing out of the catheter which is still in the patient's vein. Thus, instead of making a series of different venipunctures, only one venipuncture is made with this intravenous catheter and follow-up medication is delivered by typically injecting the follow-up medications into the hub of the catheter whereupon it is delivered to the patient. Well known and commonly used reseal plugs in the catheter hub generally provide a technique whereby the injection needle can pierce the plug, deliver the medication and, upon withdrawal of the injection needle, the reseal plug seals itself to prevent backflow of fluids out of the catheter hub. Many of the reseal plugs are made of a thin elastomeric membrane which possesses these desirable reseal properties. However, some problems have arisen when using the reseal plug technique. It has been found that the elastomeric diaphragms loose their resealing characteristics with time. When the catheter may have been on the stock shelf for a considerable period of time, there has been a tendency for the elastomeric material to take a set. When this diaphragm is pierced by the injecting needle and then withdrawn, the slit does not completely close itself whereby leakage may occur. Accordingly, the reliability of elastomeric diaphragms to prevent blood leakage from the catheter is many times in doubt.

A valving device in a blood specimen collection assembly is disclosed in U.S. Pat. No. 3,557,778. The valve in this prior assembly is a ball which is capable of moving to and from an open and closed position to prevent the backflow of testing fluid from a specimen receptacle. There is no disclosure in this prior art patent, however, on the use of such a ball valve in an intravenous catheter which is particularly used for the periodic or intermittent delivery of medication to a patient.

In addition to having an elastomeric sealing diaphragm, many intravenous catheters include a plastic, flexible catheter tube. This type catheter is inserted into the patient in conjunction with an introducer needle which facilitates the venipuncture procedure. After both the introducer needle and introducer catheter tube are positioned in the patient, the introducer needle is carefully withdrawn, leaving the catheter tube to remain in the patient's vein. Use of the plastic catheter tube is beneficial inasmuch as it minimizes trauma to the patient and also reduces risk of injury to the patient if he should suddenly move or roll over on the inserted catheter. Another problem, however, arises when using the plastic, flexible catheter tube.

When medication is to be delivered, the injection needle is usually placed into the hub of the catheter whereupon the fluid is deposited for flow through the catheter tube and on into the patient. However, inserting the injection needle too far into the hub may cause the injection needle to enter the catheter tube and perhaps damage or even puncture the wall of the plastic tube. This damage, of course, may possibly cause particles to enter the bloodstream of the patient, or if the catheter tube has been punctured, some of the medication may not reach the patient. Accordingly, it can be seen that preventative measures are required in this type catheter to prevent the injection needle from damaging or puncturing the catheter tube.

It is to the solution of preventing blood or fluids from flowing out of the catheter hub and of preventing insertion of a sharp instrument into the inside of the catheter tube which the present invention, in its various embodiments, is directed.

SUMMARY OF THE INVENTION

An intravenous catheter assembly comprises a catheter with an elongate hollow tube and a hub connected to the tube. The hub has an interior cavity communicating with the lumen of the tube and includes an aperture communicating with the cavity. A needle is slidably positioned in the aperture and the lumen of the tube so that its distal, pointed end is adapted to protrude slightly beyond the distal end of the catheter tube, with its proximal end extending beyond the aperture in the hub. Operable valve means, including a closure portion in the cavity, is adapted to close the interior entrance of the aperture under the influence of fluid flowing into the cavity from the lumen after the needle is withdrawn to thereby prevent fluid from flowing out of the hub. Included with the valve means is an activating portion located outside the exterior entrance of the aperture adapted to be moved generally axially to thereby move the closure portion away from the aperture and open the same for fluid flow into the cavity.

In the preferred embodiment of this aspect of the invention, the operable valve means is either a ball-shaped or cone-shaped element of sufficient size to seal the aperture to prevent fluid from flowing out of the cavity. In addition, the valve means serves to block the entrance of the lumen after the needle is withdrawn from the catheter tube to prevent ready re-insertion of an instrument into the lumen, but is adapted to allow flow of fluids into the lumen. The activating portion of the valve means preferably includes an arm extending through the aperture and a tab at the end of the arm which serves as a target for contact by an instrument intended to inject fluids into the hub of the catheter. Inward movement of the tab and arm along the general axial direction of the catheter moves the valve means away from the aperture thereby opening the same for the deposit of fluids into the cavity for delivery to a patient.

Another aspect of the present invention is an intravenous catheter which is substantially as described above, except that it is not used with an introducer needle as a separate, withdrawable element. In this embodiment, then, a hollow needle replaces the hollow catheter tube, the hub being directly connected to the proximal end of the needle. The hub structure and configuration and the particular valve being employed is substantially as described above and serves to prevent fluid from flowing out of the hub and in another embodiment, the valve means also serves to prevent insertion of a sharp instrument into the lumen of the needle.

In accordance with the principles of this invention, the problem of blood leakage associated with defective elastomeric diaphragm is eliminated since the instant invention does not rely upon this type of fluid closure mechanism. The valve means employed in the present invention not only effectively prevents fluids from flowing out of the catheter hub, but also may be designed to prevent an injection needle from penetrating into the lumen of the catheter tube. Thus, the valve means of the present invention offers considerably more versatility than some of the previous devices used in this type catheter. Furthermore, the activating portion of the valving approach used herein offers the advantage of direct positive movement of the valve away from the aperture so that fluid can be injected into the cavity. Positive, mechanical contact of the activating portion of the valve means outside of the aperture offers greater assurance that the aperture will be opened to thereby allow fluid into the cavity. It will be seen from a further reading of this invention, that other advantages are offered as well.

BRIEF DESCRIPTION OF THE DRAWINGS

FIG. 1 is a perspective view illustrating the preferred intravenous catheter assembly of the present invention;

FIG. 2 is a cross-sectional view taken along lines 2—2 of FIG. 1;

FIG. 3 is a partial cross-sectional view illustrating the interior of the hub of the catheter after the introducer needle has been withdrawn;

FIG. 4 is a partial cross-sectional view illustrating the interior of the hub of the catheter upon injection of a fluid medication by a syringe or like instrument; and FIG. 5 is a partial cross-sectional view similar to FIG. 2 but illustrating an alternate embodiment of the valve means within the interior of the hub.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly FIGS. 1 and 2, there is illustrated the preferred intravenous catheter assembly 10, consisting generally of two basic components, namely a catheter 12 and an introducer needle 14.

Referring to catheter 12, it includes an elongate slender hollow tube 15 having, preferably, a circular cross-section. Inasmuch as this catheter tube is intended for insertion into a patient, it is desirable to provide it with a smooth outside surface to minimize drag upon its insertion. The distal end 16 of the catheter tube has been tapered inwardly to facilitate insertion of the tube into the patient and to provide a tight fit of the tube around the introducer needle to minimize or even prevent flow of fluids into the space between the introducer needle and the catheter tube. Inside the catheter tube is a lumen 18 extending completely through the tube. At the other end of the tube, the proximal end, a hub 19 is connected. This hub is preferably a tapered female Luer connector, and includes an interior cavity 20 which communicates with lumen 18 of the catheter tube. Hub 19 also includes an open end for aperture 21, also communicating with cavity 20 and adapted to receive an injection instrument or the like for injecting fluid medicament into the hub and then on into the patient.

As seen more in FIGS. 2 and 3, a fixed insert 22 is positioned substantially transversely across cavity 20 and preferably spaced inwardly from open end 21. An aperture 24 extends through insert 22 in a direction generally parallel to the catheter tube. Inside cavity 20 in the space between the entrance 25 of lumen 18 and insert 22 is a substantially spherically shaped ball 26. The ball has a diameter greater than the diameter of aperture 24 in the insert. As a result, ball 26 serves as an operable valve adapted to close the interior entrance of the aperture under the influence of fluid flowing into cavity 20 from lumen 18. Inasmuch as fluid flow in this direction is undesirable, the valving feature serves to prevent this backflow of fluid out of the catheter hub. However, as can be seen from the drawings, ball 26 is also operable to move away from aperture 24 in order to permit flow of fluids into cavity 20.

To facilitate the operability of ball 26, an arm 28 is connected to the ball and extends through aperture 24. At the end of arm 28 is a tab 29 extending at a substantially right angle to arm 28 so as to lie generally parallel to insert 22. Tab 29 thereby serves as a target outside the exterior entrance of aperture 24 in the open end of cavity 20 the purpose of which will be discussed hereinafter.

Introducer needle 14 is assembled in catheter 12 as a package so that venipuncture may be accomplished. The introducer needle includes a long slender needle barrel 30 which is slidable positioned in and through aperture 24 in the fixed insert and also through lumen 18 in the catheter tube, so that its distal pointed end 31 protrudes slightly beyond distal end 16 of the catheter tube. Needle 31 is sufficiently long so that its proximal end extends beyond open end 21 of the hub. At the proximal end of the needle is a knob 32 which assists the operator in the sliding movement of the introducer needle particularly after venipuncture has been made and the needle is to be withdrawn. As seen in FIG. 2, needle barrel 30 may be slightly bent where it contacts ball 26; this is due to the ball size being larger than the aperture size, and presents no permanent deformation problem to the needle inasmuch as the needle is generally resilient under bending stresses.

During use of this catheter assembly, venipuncture is made by inserting the combined introducer needle and catheter into the vein of the patient with point 31 of the needle facilitating this insertion. After the catheter assembly is in position, the operator slowly withdraws introducer needle 14 out of the catheter while leaving catheter tube 15 in the vein of the patient. This withdrawal condition is illustrated in FIG. 3. It can be appreciated that withdrawing the needle from the catheter causes blood to flow into lumen 18 toward the catheter hub. Once the introducer needle has been completely withdrawn, flow of this blood, or other fluids, out of the hub is prevented by the valving device in the cavity of the hub. Specifically, the flow of blood as indicated by arrows B in FIG. 3 urges ball 26 against the interior entrance of aperture 24 to effect a closure thus preventing outflow of blood from the hub. With this closure in effect, the catheter may remain inserted in the patient for intermittent use over a prolonged period of time. This is significantly more desirable than effecting a number of venipunctures in the patient each time medication has to be delivered.

When the need for delivering medication arises, the operator uses a suitable injection device to deposit the fluid medication into the catheter hub for delivery to the patient as illustrated in FIG. 4. A syringe 32 or like device, preferably with a mating male Luer connection specifically adapted for insertion into the female Luer connection serving as hub 19, is placed into the open end of the hub. As syringe 32 is moved further into the open end of the hub, its front face 34 contacts target tab 29; deeper movement of syringe 32 moves the valving device, including tab 29, arm 28 and ball 26, in a generally axial direction. As a result, ball 26 is moved away from aperture 24 to open the same and thereby allow fluid flow into cavity 20. This fluid flow of medication is indicated by arrows M in FIG. 4. It is noted that tab 29 abuts against insert 22 which thereby prevents ball 26 from moving too deeply into cavity 20 toward entrance 25 of lumen 18. Accordingly, the valving device is effectively and positively opened so that fluid medication can be injected into the hub for delivery to the patient. It can be appreciated that once syringe 32 is withdrawn from the hub, the valving ball 26 is adapted to close again to prevent undesirable outflow of blood.

An alternate embodiment of the valving device is illustrated in FIG. 5 wherein the remaining elements of the catheter assembly are the same as in the previously described embodiment. Instead of a ball for effecting closure of the interior entrance of the fixed insert, a cone-shaped valve 36 is employed. The cone is positioned so that its narrow taper extends toward aperture 24a. The wider or base portion of cone 36 has a diameter larger than the diameter of aperture 24a so that an effective fluid closure can be accomplished. It is clear that fluid backflowing through lumen 18a into cavity 20a will urge tapered cone 36 into aperture 24a thereby closing the same to prevent flow of fluids therethrough. This cone valve is operably open in substantially the same manner as described above. Other configurations of the valve are within the purview of this concept and may be utilized in accordance with the choice of the designer.

In the preferred embodiment of the present invention, the closure portion of the valving device, whether it be the ball, cone or otherwise, is fabricated to be of sufficient size and shape to block the entrance of the lumen after the needle has been withdrawn from the catheter to prevent ready re-insertion of an instrument into the lumen. As noted when describing FIG. 2 above, upon original packaging when the introducer needle is positioned in the catheter tube, it is slightly bent due to the size of the ball near the aperture. Thus, the valving device, including the connected arm and tab makes it difficult to readily re-insert a needle or other injection instrument into the lumen of the catheter tube.

When employing an introducer needle to effect venipuncture, the catheter tube is preferably made of a flexible, plastic material. This is convenient for the patient and also is convenient from the manufacturing standpoint. However, there are instances when the catheter assembly is used without an introducer needle which is to be withdrawn after venipuncture. In that case, an elongate hollow needle having a pointed distal end replaces the catheter tube as described hereinbefore. The hub is directly connected to the hollow needle, with the valving device and all of its features being the same as hereinbefore described. Venipuncture is effected merely by inserting the hollow needle, generally a rigid, smooth surfaced metal, into the vein of the patient. The valve element of this assembly then immediately takes effect since blood starts to flow through the hollow needle toward the open end of the catheter. Thus, it can be seen that whether an intravenous catheter assembly with an introducer needle is used, or a catheter assembly with a hollow needle is employed, the same desirable valving advantages are realized.

I claim:

1. An intravenous catheter assembly comprising:
   a catheter comprised of an elongated, hollow tube and a hub connected at one end of said tube, the other end of said tube being an open end,
   said hub having an interior cavity communicating with the lumen of said tube;
   a fixed insert located substantially transversely across said cavity and having an aperture therethrough generally parallel to said catheter tube the periphery of said aperture forming a valve seat;
   a needle slideably positioned in said aperture and the lumen of said tube, the distal, pointed end of the needle adapted to protrude slightly beyond the distal end of said catheter tube, the proximal end of said needle extending beyond the open end of said hub;
   valve seat closure means in said cavity and operatively associated with said valve seat and disposed between said insert and the entrance to said lumen;
   valve seat opening means connected to said valve seat closure means and extending through said aperture to the opposite side of said insert;
   said needle displacing said valve seat closure means from said seat while said needle is positioned in said catheter;
   said valve seat closure means adapted to close said aperture to prevent backflow from said lumen after said needle is withdrawn;
   said valve seat opening means adapted to displace said valve seat closure means from said seat and provide access for the deposit of fluids into said lumen for delivery to the patient; and,
   said valve seat closure means and said valve seat opening means cooperatively preventing the ready reinsertion of an instrument into said lumen after said needle has been withdrawn.

2. An intravenous catheter assembly as defined in claim 1 wherein said operable valve means is a ball of sufficient size to close the aperture to prevent fluid flow therethrough.

3. An intravenous catheter assembly as defined in claim 1 wherein said operable valve means is cone-shaped with a narrow taper extending toward said aperture so that the aperture can be closed to prevent fluid flow therethrough.

4. An intravenous catheter assembly as defined in claim 1 wherein said connected means for moving said valve means includes an arm extending through said aperture and connected to a tab extending generally parallel to said insert to serve as a target whereby inward movement of the tab and arm along the general axial direction of said catheter moves said valve means away from said aperture thereby opening the same for the deposit of fluids into the cavity for delivery to a patient.

5. An intravenous catheter assembly comprising:
   a catheter comprised of an elongated, hollow tube and a hub connected to said tube and having an interior cavity communicating with the lumen of said tube, said hub including an aperture aligned axially with said catheter lumen and communicating with said cavity, the periphery of said aperture forming a valve seat;

a needle slideably positioned in said aperture and in the lumen of said tube, the distal, pointed end of said needle protruding slightly beyond the distal end of said catheter tube, and the proximal end of the needle extending beyond the aperture in the hub in position for making the initial veni-puncture for introducing the catheter into the patient;

valve means cooperatively associated with said valve seat but displaced therefrom by said needle when said needle is in place in said lumen to make said initial venipuncture, said valve means including a closure portion in said cavity adapted to close the interior entrance of said aperture to prevent backflow after said needle is withdrawn, said valve means including an activating portion located outside the interior entrance of said aperture adapted to displace said valve means closure portion from said seat and provide access for the deposit of fluids into said lumen for delivery to the patient said valve means and said activating portion cooperatively preventing the ready reinsertion of an instrument into said lumen after said needle has been withdrawn.

6. The intravenous catheter assembly as defined in claim 5 further including:

an insert, disposed substantially transversely across said cavity, and wherein said aperture is disposed in said insert;

and wherein said valve means closure portion is disposed between said insert and the entrance of said lumen.

7. The intravenous catheter assembly as defined in claim 6 wherein said valve means activating portion includes an arm extending through said aperture;

a target tab connected to the end of said arm and disposed outside said cavity and adapted to cooperatively engage a medicament-containing instrument and displace said valve means closure portion from said valve seat when said medicament-containing instrument is inserted into said hub to provide access for the deposit of said medicament into said lumen for delivery to the patient.

8. The intravenous catheter assembly as defined in claim 7 wherein the length of said arm is shorter than the axial extent of said cavity so that said valve means does not occlude the entrance to said lumen when said valve means closure portion is displaced from said valve seat by the insertion of said medicament-containing instrument into cooperative engagement with said tab.

* * * * *